United States Patent
Zhuo et al.

(10) Patent No.: US 11,645,748 B2
(45) Date of Patent: May 9, 2023

(54) THREE-DIMENSIONAL AUTOMATIC LOCATION SYSTEM FOR EPILEPTOGENIC FOCUS BASED ON DEEP LEARNING

(71) Applicant: ZHEJIANG UNIVERSITY, Hangzhou (CN)

(72) Inventors: Cheng Zhuo, Hangzhou (CN); Mei Tian, Hangzhou (CN); Hong Zhang, Hangzhou (CN); Qinming Zhang, Hangzhou (CN); Teng Zhang, Hangzhou (CN); Yi Liao, Hangzhou (CN); Xiawan Wang, Hangzhou (CN); Jianhua Feng, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 17/047,392

(22) PCT Filed: Aug. 30, 2019

(86) PCT No.: PCT/CN2019/103530
§ 371 (c)(1),
(2) Date: Oct. 14, 2020

(87) PCT Pub. No.: WO2020/224123
PCT Pub. Date: Nov. 12, 2020

(65) Prior Publication Data
US 2022/0230302 A1 Jul. 21, 2022

(30) Foreign Application Priority Data
Jun. 24, 2019 (CN) .......................... 201910549416.1

(51) Int. Cl.
G06T 7/00 (2017.01)
G06V 10/764 (2022.01)
A61B 6/03 (2006.01)

(52) U.S. Cl.
CPC ............ G06T 7/0012 (2013.01); A61B 6/032 (2013.01); A61B 6/037 (2013.01); G06V 10/764 (2022.01);
(Continued)

(58) Field of Classification Search
CPC ......... G06T 7/0012; G06T 2207/10104; G06T 2207/20081; G06T 2207/20084;
(Continued)

(56) References Cited

U.S. PATENT DOCUMENTS

| | | | |
|---|---|---|---|
| 2016/0116603 A1* | 4/2016 | Chen | G01T 1/1603 250/362 |
| 2019/0130569 A1 | 5/2019 | Liu et al. | |
| 2019/0247662 A1* | 8/2019 | Poltroak | A61B 5/0816 |

FOREIGN PATENT DOCUMENTS

| | | |
|---|---|---|
| CN | 107403201 A | 11/2017 |
| CN | 108629784 A | 10/2018 |

(Continued)

OTHER PUBLICATIONS

International Search Report (PCT/CN2019/103530); dated Mar. 5, 2020.

*Primary Examiner* — Siamak Harandi
(74) *Attorney, Agent, or Firm* — W&G Law Group

(57) ABSTRACT

The present disclosure discloses a three-dimensional automatic location system for an epileptogenic focus based on deep learning. The system includes: a PET image acquisition and labelling module; a registration module mapping PET image to standard symmetrical brain template; a PET image preprocessing module generating mirror image pairs of left and right brain image blocks; a network SiameseNet training module containing two deep residual convolutional neural networks which share weight parameters, an output layer connecting a multilayer perceptron and a softmax layer, and using a training set of an epileptogenic focus image and an
(Continued)

normal image to train the network to obtain a network model; a classification module and epileptogenic focus location module, using the trained network model to generate a probabilistic heatmap for the newly input PET image, a classifier determining whether the image is normal or epileptogenic focus sample, and then predicting a position for the epileptogenic focus region.

9 Claims, 4 Drawing Sheets

(52) U.S. Cl.
CPC ............ *G06T 2207/10104* (2013.01); *G06T 2207/20081* (2013.01); *G06T 2207/20084* (2013.01)

(58) Field of Classification Search
CPC . G06T 7/70; G06T 2207/30016; A61B 6/032; A61B 6/037; A61B 6/5211; A61B 6/501; A61B 6/5217; G06V 10/764; G06V 10/454; G06V 2201/03; G06V 10/255; G06V 10/82; G06N 3/045; G06N 3/082; G06F 18/214; G16H 30/40
See application file for complete search history.

(56) References Cited

FOREIGN PATENT DOCUMENTS

| | | |
|---|---|---|
| CN | 109447996 A | 3/2019 |
| CN | 109523521 A | 3/2019 |
| CN | 109754387 A | 5/2019 |

* cited by examiner

THREE-DIMENSIONAL AUTOMATIC LOCATION SYSTEM FOR EPILEPTOGENIC FOCUS BASED ON DEEP LEARNING

CROSS-REFERENCE TO RELATED APPLICATIONS

The present application is based on International Application No. PCT/CN2019/103530, filed on Aug. 3, 2019, which claims priority to Chinese Patent Application No 201010549416.1, filed on Jun. 24, 2019, the contents of which are incorporated herein by reference in their entireties.

TECHNICAL FIELD

The present disclosure relates to the technical field of medical imaging engineering, and in particular, to a three-dimensional automatic location system for an epileptogenic focus based on deep learning.

BACKGROUND

With the development of medical imaging technology and artificial intelligence technology, automatic and semi-automatic computer-aided diagnosis systems are widely used in precision diagnosis and treatment to improve diagnosis accuracy and prognosis. At present, detection systems aiming at epilepsy include positron emission computed tomography (PET), nuclear magnetic resonance imaging (MRI), single photon emission computed tomography (SPECT) and electroencephalography (EEG), in which the PET has higher sensitivity for the detection and prognosis of epilepsy. For determination of types of epilepsy, surgical treatment of refractory epilepsy, etc., it is necessary to use a diagnostic system to accurately locate a position of an epileptogenic focus. However, conventional routine clinical diagnosis of visual evaluation of three-dimensional PET images is very time-consuming and affected by clinical experience of a doctor. Therefore, it is very important to propose an accurate and rapid epileptogenic focus location system.

Challenges faced by existing technologies are mainly as follows: 1. imaging technology usually judges abnormalities based on statistical inference of standard uptake values (SUV) and/or asymmetry index (AI) of regions or voxels. Regional statistical methods usually divide a brain into larger regions of interest (ROI) and then compare an average value of SUV or AI in the region. Since the region is often much larger than a lesion region, this method will ignore subtle changes, resulting in reduction in its detection sensitivity. Voxel statistical methods usually use a statistical parameter mapping (SPM) software to compare data from individual cases and a control group, but the voxel statistical methods are highly sensitive to registration errors so that it is to generate false positives in misaligned regions. 2. Most of existing algorithms are only suitable for two-dimensional natural image processing, while since the PET imaging is a three-dimensional structure composed of parallel scanning image frames, a two-dimensional location algorithm will ignore important inter-frame information. 3. Due to problems of a small amount of medical image data, lack of high-quality labeled data and training samples, and imbalance of samples caused by a large difference in the number of positive and negative samples, etc., the trained model may be overfitting or a model generalization ability is not high.

In summary, providing a three-dimensional automatic location system for an epileptogenic focus region, which uses symmetry information within and between frames of the PET image to improve accuracy and efficiency of the epileptogenic focus location, has become an important technical problem to be solved urgently.

SUMMARY

In view of shortcomings of the current medical image lesion location technology, an object of the present disclosure is to provide a three-dimensional location system for a brain epileptogenic focus in a region based on deep learning, for automatically locating a position of the brain epileptogenic focus, with accuracy of location results being high and robustness of the model being relatively high.

The object of the present disclosure is achieved by a following technical aspect: a three-dimensional automatic location system for an epileptogenic focus based on deep learning, and the system includes following modules:

(1) a PET image acquisition and labelling module, including image acquisition and epileptogenic focus region labelling:

1.1) acquiring an image: using a 3D PET/CT scanner to acquire a PET image of a brain, a subject maintaining the same posture during an acquisition process, acquiring the PET image. After the image is acquired, image format conversion is performed, that is, an originally acquired image sequence in a DICOM format is converted into an easy-to-process image in a NIFTI format.

1.2) labelling samples: dividing the PET images into a normal sample set and an epileptogenic focus sample set, and manually labelling the epileptogenic focus region for the epileptogenic focus sample set, where the epileptogenic focus region is labelled as 1, and the remaining regions are labelled as 0.

(2) a PET image registration module: using cross-correlation as the similarity measure between images, using a symmetric differential homeomorphic (SyN) algorithm to deform all PET images and the labelled images thereof into the same symmetric standard space, in order to achieve the registration from the acquired PET images and the labelled images to standard symmetric brain templates.

After registration, a Gaussian smoothing algorithm is used to reduce registration errors caused by individual differences. The Gaussian smoothing process selects the FWHM of the full width at half maximum of the Gaussian function to be 5 to 15 mm. Z-score normalization is performed on the smoothed image.

(3) adopting a deep learning system based on symmetry, including following modules:

3.1) a data preprocessing module:

3.1.1) data enhancement: performing radial distortion and image intensity enhancement on the registered image and the label to obtain a newly generated image and label. The radial distortion is that an image pixel point takes a distortion center as a center point, deviation is generated along a radial position, and a calculation process of the radial distortion is:

$$P_u = P_d + (P_d - P_c)(k_1 r^2 + k_2 r^4 + k_3 r^6 + \ldots)$$

where $P_u$ is a pixel point of the original image, $P_d$ is a pixel point of the distorted image, $P_c$ is a distortion center, $k_i (i=1,2,3 \ldots)$ is a distortion coefficient of the radial distortion, and $r$ is a distance between $P_d$ and $P_c$ in a vector space.

The image intensity enhancement includes filter processing, image noise-adding processing, and multiplicative and additive transformation of image gray values in the space, and a formula for the image intensity enhancement is:

$$P_a = g\_mult \times P_u + g\_add$$

where $P_a$ is an image pixel point after the image intensity enhancement, g_mult is an image pixel point of a multiplicative Gaussian bias field, and g_add is an image pixel point of an additive Gaussian bias field.

3.1.2) image block division: performing image block division on enhanced image data, using a three-dimensional sliding window to divide left and right hemispheres L and R of the PET image into mirror image pairs of the image block, and dividing data of the mirror image pairs of the image block into a training set, a verification set and a test set according to proportions; the training set, the verification set and the test set all contain two types of PET image block data—epileptogenic focus and normal. In the image data set, resolution of each PET image data is X×Y×Z pixels, a size of the sliding scanning window block is set to m×m×m, and a sliding step length is set to t. Then, the size of each image block is m×m×m. For the left and right hemispheres of a PET image, it can be divided into $$\frac{\frac{X}{2}-m}{t} \times \frac{Y-m}{t} \times \frac{Z-m}{t}$$

pairs of image blocks.

3.2) a network building module: building a deep network SiameseNet. This network contains two identical convolutional neural networks, a fully connected layer and an output layer. Each of the convolutional neural networks has a structure of ten layers, in which the first layer includes one convolution layer (conv), one batch normalization operation unit (batch normalization), one Relu function, and one pool layer (pool) that are connected in sequence; each of the second to the ninth layers is a ResBlock, and each of the ResBlocks contains two convolution layers, two normalization operations and one Relu function that are connected in sequence; the tenth layer is one convolution layer, and the tenth layers of the two convolutional neural networks output and are connected to one fully connected layer (fc) for nonlinear transformation. Finally, one output layer is connected.

The two convolutional neural networks of the SiameseNet share the same weight parameter θ in each layer and the inputs of the network are mirror image pairs of a pair of image blocks, to obtain a feature L_feature and a feature R_feature of two high-dimensional images. An absolute difference of the two high-dimensional image features is calculated: d=|L_feature−R_feature|, and it is transmitted to a multi-layer perceptron (MLP) of the fully connected layer for probability regression. Dimensions of the fully connected layer vector are 2048, 1024, 512 and 2 in sequence. The dropout layer is used in the middle of the fully connected layer and p=0.5 is set, to reduce network parameters and prevent overfitting. The output layer uses a classification probability of a softmax regression function, that is, a probability that the image block carries the epileptogenic focus or is normal.

In the model training, a cross entropy function is used as a loss function of the network. A calculation method of the cross entropy Loss (a, b) is:

$$\text{Loss}(a, b) = -\sum_{i=1}^{n} a_i \ln b_i$$

where n represents the number of samples, a is correct probability distribution, and b is probability distribution predicted by the network model. Standard stochastic gradient descent (SGD) is used to update the weight parameter θ, and a formula thereof is:

$$\theta^k = \theta^{k-1} - \eta \frac{d}{d\theta^{k-1}} \text{Loss}(a, b)$$

where η is a learning rate and $\theta^k$ is a k-th weight parameter.

3.3) a test image detection module:

image classification: using the trained model to calculate a probability heatmap of the PET image of the test set. The probability heatmap is a probability map stitched by corresponding probabilities of different image blocks on one PET image, and a size is $$\frac{X-m}{t} \times \frac{Y-m}{t} \times \frac{Z-m}{t}.$$

Afterwards, a logistic regression algorithm is used to classify the probability heatmap corresponding to each PET image, to obtain a classification result, that is, the normal PET image or the epileptogenic focus PET image.

Locating of the epileptogenic focus: performing bilinear interpolation on the probabilistic heatmap identified as the epileptogenic focus PET image, changing the probability heatmap to a size of the original image, and predicting a region larger than a probability threshold as the epileptogenic focus region.

Beneficial effects of the present disclosure are as follows.

1) It can automatically learn deep features in the PET image data. The traditional visual assessment requires a doctor to observe and judge frame by frame, which is extremely dependent on experience and technical level of the doctor and consumes a lot of time. The SiameseNet can automatically learn high-dimensional asymmetric features in PET images to discover internal relationship between the PET image and the epileptogenic focus. Compared with the traditional location system for the epileptogenic focus, the system proposed by the present disclosure can learn high-order features that are difficult for human eyes to recognize, and it also takes into account the a priori knowledge of asymmetric metabolic distribution in patients having unilateral epilepsy.

2) It can achieve precise locating of the lesion region. The system proposed by the present disclosure can accurately detect images of patients having abnormal metabolism, and compared with the existing SPM software, the epileptogenic focus region predicted by the system is more consistent with a physician's visual assessment and maintains relatively high accuracy and efficiency. Therefore, it has relatively high value in helping doctors locate the epileptogenic region and follow-up surgical treatment.

3) It can be applied to detection of the epileptogenic focus in different brain regions. The system proposed by the present disclosure is effective for the detection of epileptogenic focus in different brain regions of the whole brain and is suitable for epileptic patients having epileptogenic focus in different brain regions.

4) Network training with a small data volume can be achieved. The present disclosure utilizes image enhancement and mirror image pairs for division of the image blocks to increase the sample amount, based on which training model and testing data are performed, thereby avoiding overfitting of network training and improving the robustness of the network training. In addition, in order to balance samples of normal and patient data, the present disclosure uses sample weighting as data enhancement and sets a relatively large weight for a small number of samples, to balance a proportion of normal region samples with a proportion of epileptogenic region samples in each batch during training.

DESCRIPTION OF EMBODIMENTS

The present disclosure will be further described in detail below with reference to the drawings and specific embodiments.

Figure 1:
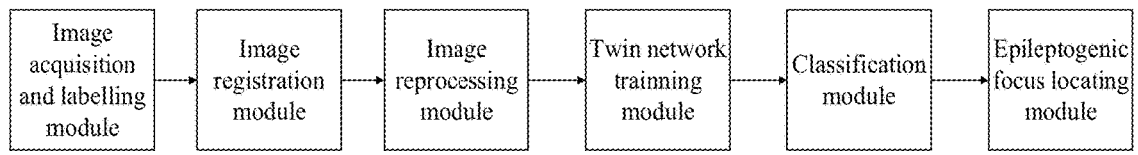
FIG. 1 is a structural block diagram of a three-dimensional location system for an epileptogenic focus based on deep learning according to an embodiment of the present disclosure.
Figure 2:
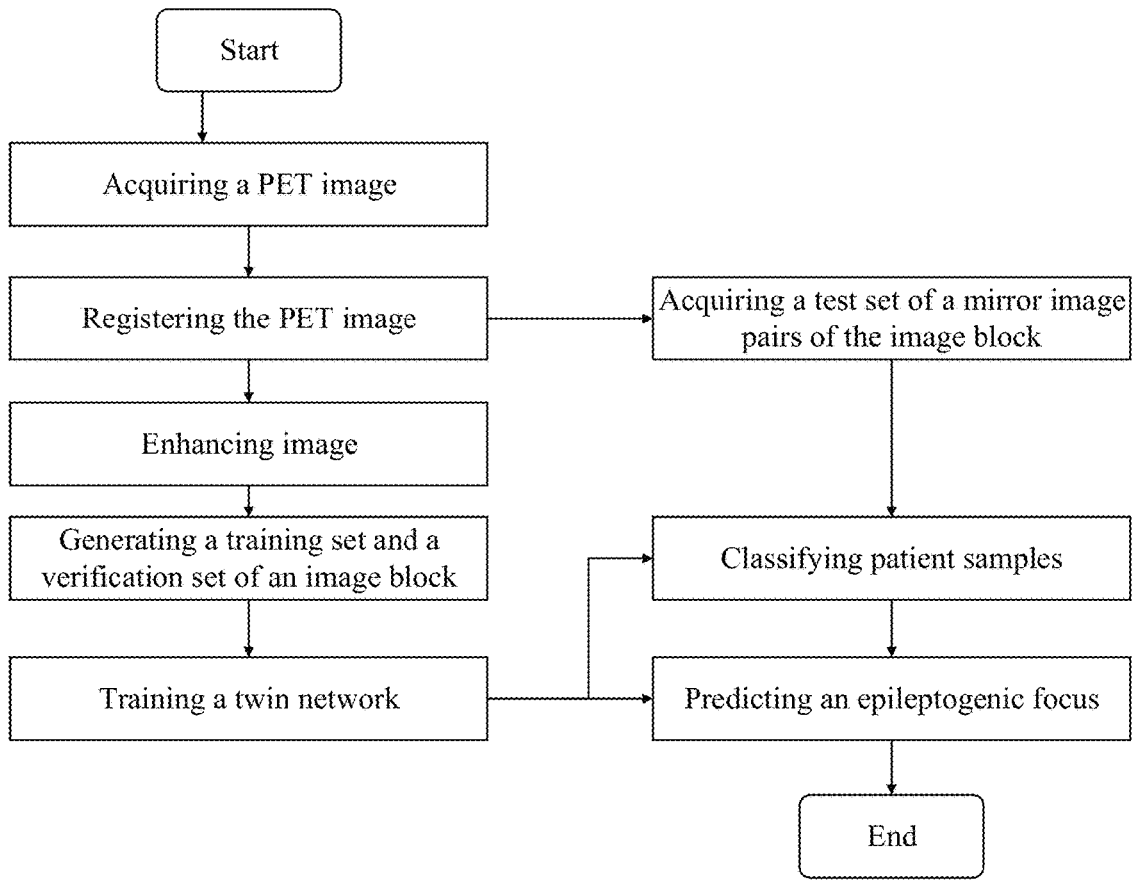
FIG. 2 is a flowchart of implementation of a three-dimensional location system for an epileptogenic focus based on deep learning according to an embodiment of the present disclosure.

As shown in FIG. 1, the three-dimensional automatic location system for an epileptogenic focus according to an embodiment of the present disclosure includes following modules:

(1) a PET image acquisition and labelling module, including image acquisition and epileptogenic focus region labelling:

1.1) acquiring an image: using a 3D PET/CT scanner to acquire a PET image of a brain, a subject maintaining the same posture during an acquisition process, acquiring the PET image. After the image is acquired, image format conversion is performed, that is, an originally acquired image sequence in a DICOM format is converted into an easy-to-process image in a NIFTI format.

1.2) labelling samples: dividing the PET images into a normal sample set and an epileptogenic focus sample set, and manually labelling the epileptogenic focus region for the epileptogenic focus sample set, where the epileptogenic focus region is labelled as 1, and the remaining regions are labelled as 0.

(2) a PET image registration module: using cross-correlation as the similarity measure between images, using a symmetric differential homeomorphic (SyN) algorithm to deform all PET images and the labelled images thereof into the same symmetric standard space, in order to achieve the registration of the acquired PET images, the labelled images and standard symmetric brain templates. For deforming an original image I to an image J, a following objective function is minimized:

$$f = \operatorname{argmin}\left\{\int_0^1 \|Lv\|^2 dt + \lambda \int_\Omega C(I,J)d\Omega\right\}$$

The first term is a smoothing term, in which L is a smoothing operator and v is a velocity field. $\lambda$ in the second term controls accuracy of matching. $C(I,J)$ is a similarity measure, where $C(I,J)$ can be expressed as:

$$C(I,J) = \frac{\langle I,J\rangle^2}{\langle I\rangle\langle J\rangle}$$

After registration, a Gaussian smoothing algorithm is used to reduce registration errors caused by individual differences. The Gaussian smoothing process selects the FWHM of the full width at half maximum of the Gaussian function to be 5 to 15 mm, to eliminate the registration errors caused by individual differences. Z-score normalization is performed on the smoothed image:

$$z = \frac{J - \mu}{\sigma}$$

where $\mu$ is mean of the registered image J, and $\sigma$ is variance of an image.

(3) adopting a deep learning system based on symmetry, including following modules:

3.1) a data preprocessing module:

3.1.1) data enhancement: performing radial distortion and image intensity enhancement on the registered image and the label to obtain a newly generated image and label. The radial distortion is that an image pixel point takes a distortion center as a center point, deviation is generated along a radial position, and a calculation process of the radial distortion is:

$$P_u = P_d + (P_d - P_c)(k_1 r^2 + k_2 r^4 + k_3 r^6 + \ldots)$$

where $P_u$ is a pixel point of the original image, $P_d$ is a pixel point of the distorted image, $P_c$ is a distortion center, $k_i (i=1,2,3 \ldots)$ is a distortion coefficient of the radial distortion, and r is a distance between $P_d$ and $P_c$ in a vector space.

The image intensity enhancement includes filter processing, image noise-adding processing, and multiplicative and additive transformation of image gray values in the space, and a formula for the image intensity enhancement is:

$$P_a = g\_mult \times P_u + g\_add$$

where $P_a$ is an image pixel point after the image intensity enhancement, g_mult is an image pixel point of a multiplicative Gaussian bias field, and g_add is an image pixel point of an additive Gaussian bias field.

3.1.2) image block division: performing image block division on enhanced image data, using a three-dimensional sliding window to divide left and right hemispheres L and R of the PET image into mirror image pairs of the image block, and dividing data of the mirror image pairs of the image block into a training set, a verification set and a test set according to proportions; the training set, the verification set and the test set all contain two types of PET image block data—epileptogenic focus and normal. In the image data set, resolution of each PET image data is X×Y×Z pixels, a size of the sliding scanning window block is set to m×m×m, and a sliding step length is set to t. Then, the size of each image block is m×m×m. For the left and right hemispheres of a PET image, it can be divided into $$\frac{\frac{X}{2}-m}{t} \times \frac{Y-m}{t} \times \frac{Z-m}{t}$$

pairs of image blocks.

3.2) a network building module: building a deep twin network SiameseNet. This network contains two identical convolutional neural networks, a fully connected layer and an output layer. Each of the convolutional neural networks has a structure of ten layers, in which the first layer includes one convolution layer (cony), one batch normalization operation unit (batch normalization), one Relu function, and one pool layer (pool) that are connected in sequence; each of the second to the ninth layers is a ResBlock, and each of the ResBlocks contains two convolution layers, two normalization operations and one Relu function that are connected in sequence; the tenth layer is one convolution layer, and the tenth layers of the two convolutional neural networks output and are connected to one fully connected layer (fc) for nonlinear transformation. Finally, one output layer is connected. Parameter setting for one random dropout can be 0.5.

In the SiameseNet network model, a calculation process of the convolution layer operation is:

$$output_{conv} = \frac{input_{conv} + 2 \times pad - kernal}{stride} + 1$$

where $output_{conv}$ is the three-dimensional size of output image data of each of the convolution layer (length, width and depth of the image), $input_{conv}$ is a three-dimensional size of an input image, pad means to fill pixels around the image, kernal is a three-dimensional size of a convolution kernel, and stride is a step length of the convolution kernel.

For each of the convolution layers, the batch normalization operation is used, to accelerate a convergence speed and stability of the network, and a formula for the batch normalization operation is:

$$\widehat{input_{norm}} = \frac{input_{norm} - \mu}{\sqrt{\sigma^2 + \epsilon}}$$
$$output_{norm} = \gamma \widehat{input_{norm}} + \beta$$

where $input_{norm}$ is each batch data that is input, $\widehat{input_{norm}}$ is normalized data, $output_{norm}$ is batch data output by the batch normalization operation, $\mu$ and $\sigma$ are respectively mean and variance of each batch data, $\gamma$ and $\beta$ are respectively scaling and translation variables, and $\epsilon$ is a relatively small constant data added to increase training stability;

an activation function connected to each of the convolution layers uses the Relu function, which can shorten a training period, and a calculation method of the Relu function is:

$$output_{relu} = max(input_{relu}, 0)$$

where $input_{relu}$ is input data of the Relu function, and $output_{relu}$ is output data of the Relu function.

Figure 3:
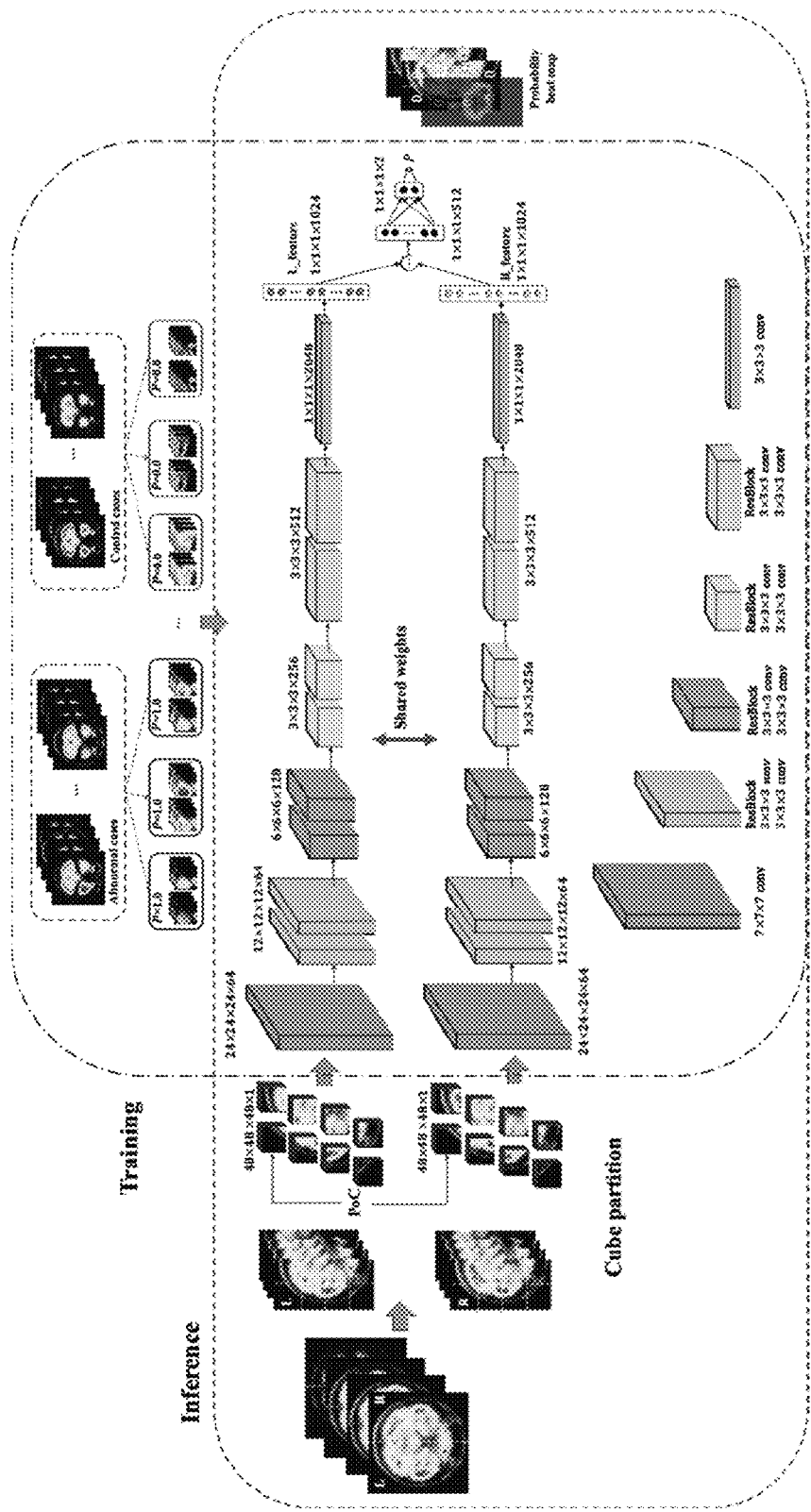
FIG. 3 is a schematic diagram of building of a deep SiameseNet according to an embodiment of the present disclosure.

The two convolutional neural networks of the SiameseNet share the same weight parameter θ in each layer and the inputs of the network are mirror image pairs of a pair of image blocks. As shown in FIG. 3, the size of the input image block is 48×48×48×1, where 48×48×48 represents the length, width and height of the image block, 1 represents the number of channels of the image block. After the convolution of the first layer, a resulting feature size is 24×24×24× 64, and feature sizes respectively obtained through Res-Blocks are 12×12×12×64, 12×12×12×64, 6×6×6×128, 6×6× 6×128, 3×3×3×256, 3×3×3×256, 3×3×3×512 and 3×3×3× 512 . After the tenth convolution layer, two high-dimensional features L_feature and R_feature having a size of 1×1×1×2048 are obtained. An absolute difference of the two high-dimensional image features is calculated: d=|L_feature−R_feature|, and it is transmitted to a multi-layer perceptron (MLP) of the fully connected layer for probability regression. Dimensions of the fully connected layer vector are 1×1×1×1024, 1×1×1×512 and 1×1×1×2 in sequence. The dropout layer is used in the middle of the fully connected layer and p=0.5 is set, to reduce network parameters and prevent overfitting. The output layer uses a classification probability of a softmax regression function, that is, a probability that the image block carries the epileptogenic focus or is normal, and a formula of softmax is:

$$Softmax(d) = \frac{e^{d_j}}{\sum_g e^{d_j}}$$

where $d_j$ represents output of different categories, g represents the number of the categories, j=1,2, ... g.

In the model training, a cross entropy function is used as a loss function of the network. A calculation method of the cross entropy Loss(a, b) is:

$$Loss(a, b) = -\sum_{i=1}^{n} a_i \ln b_i$$

where n represents the number of samples, a is correct probability distribution, and b is probability distribution predicted by the network model. Standard stochastic gradient descent (SGD) is used to update the weight parameter θ, and a formula thereof is:

$$\theta^k = \theta^{k-1} - \eta \frac{d}{d\theta^{k-1}} Loss(a, b)$$

where η is a learning rate and $\theta^k$ is a k-th weight parameter.

Figure 4:
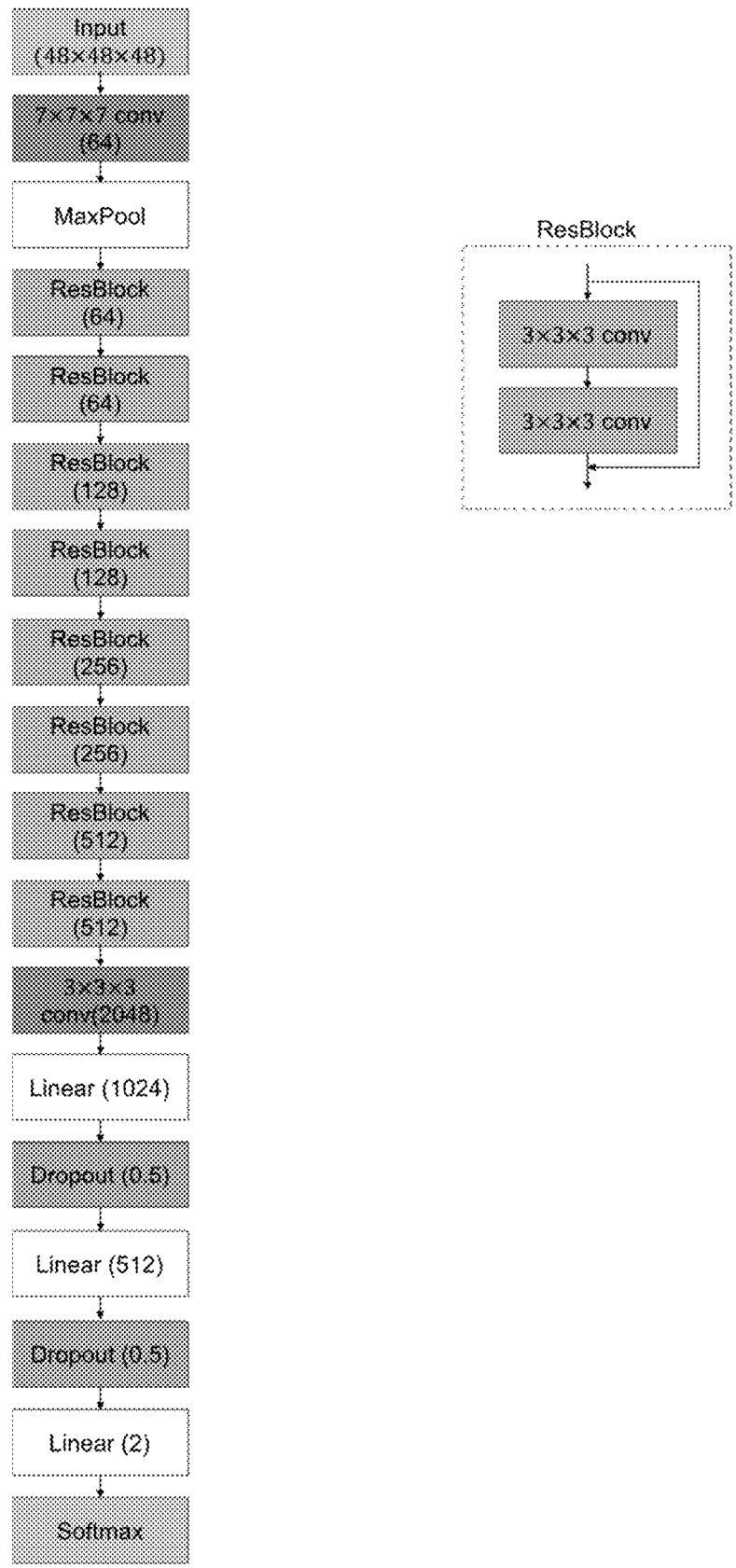
FIG. 4 is a structural schematic diagram of a single residual neural network of SiameseNet according to the present disclosure.

In an example of the present disclosure, flowcharts of the training phase and the test phase are as shown in FIG. 4, a basic network framework adopted by SiameseNet is ResNet18, and the two ResNets share the same network weight parameter θ. The network is trained using a training set of the epileptogenic focus PET image and the normal image, and a network model is obtained through the training process. In addition, a small number of mirror image pairs of an image background block are added to the normal samples of the training set, to reduce impact of the image background on the model.

Figure 5:
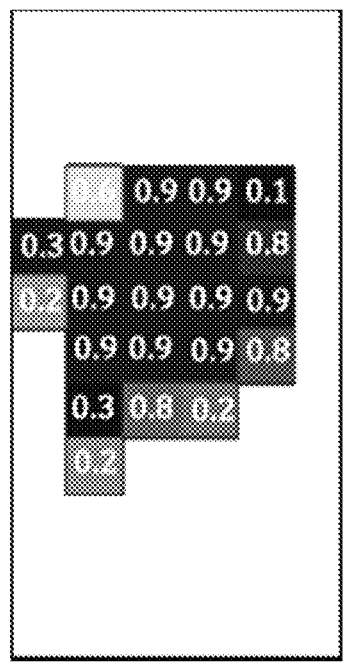
FIG. 5 is a probability heatmap corresponding to a PET image according to an embodiment of the present disclosure.

3.3) a test image detection module:
   image classification: using the trained model to calculate a probability heatmap of the PET image of the test set. As shown in FIG. 5, the probability heatmap is a probability map stitched by corresponding probabilities of different image blocks on one PET image, and a size is $$\frac{X-m}{t} \times \frac{Y-m}{t} \times \frac{Z-m}{t}.$$

Afterwards, a logistic regression algorithm is used to classify the probability heatmap corresponding to each PET image, to obtain a classification result, that is, the normal PET image or the epileptogenic focus PET image.

Locating of the epileptogenic focus: performing bilinear interpolation on the probabilistic heatmap identified as the epileptogenic focus PET image, changing the probability heatmap to a heatmap having the same size as that of the original image, and predicting a region larger than a probability threshold as the epileptogenic focus region. A calculation formula of the bilinear interpolation is:

$$f(m+u, n+v)=(1-u)(1-v)f(m, n)+u(1-v)f(m+1, n)+(1-u)vf(m, n+1)+uvf(m+1, n+1)$$

where f(m+u, n+v) is a newly calculated pixel value, f(m, n), f(m+1, n), f(m, n+1) and f(m+1, n+1) are respectively four original pixel values around the new pixel value, and u and v are distances between the original pixel point and the new pixel point. By setting the threshold k (heatmap≥heatmap_max×k), in which the heatmap_max is the maximum value of the heatmap, the predicted epileptogenic focus region is finally obtained.

In a specific case where the system of this embodiment is applied, as shown in FIG. 4, firstly, an acquired PET data set is divided into a training set, a verification set and a test set, a twin network learning system is used to extract two feature vectors of left and right brain image blocks, an absolute difference between the two feature vectors is calculated, and then a multi-layer perceptron is added for probability regression. Finally, a sliding window block is used for scanning test on each entire image, a probability heatmap is output after scanning, and finally a detection result map is obtained, so as to achieve classification and locating of an epileptogenic focus in the PET image. Finally, AUC of a classification result of the entire image is 94%. In addition, compared with an existing SPM software, the epileptogenic focus region predicted by the system is more consistent with a physician's visual assessment and maintains a higher accuracy and efficiency.

This patent is not limited to the preferred embodiment above. Under inspiration of this patent, anyone can obtain various other forms of epileptogenic focus location system based on deep learning, and all changes and modifications made in accordance with the scope of the patent application of the present disclosure shall fall within the scope of this patent.

What is claimed is:

1. A three-dimensional automatic location system for an epileptogenic focus based on deep learning, wherein the system comprises following modules:
   (1) a PET image acquisition and labelling module, for image acquisition and epileptogenic focus region labelling:
   1.1) acquiring an image: a subject using a 3D brain image acquisition on a PET scanner, to acquire the PET brain image at the same posture state process;
   1.2) labelling samples: dividing the PET images into a normal sample set and an epileptogenic focus sample set, and manually labelling an epileptogenic focus region for the epileptogenic focus sample set, where the epileptogenic focus region is labelled as 1, and remaining regions are labelled as 0;
   (2) a PET image registration module: using cross-correlation as similarity measure between an original image and a registration image, using a symmetric differential homeomorphic (SyN) algorithm to register all of the PET images and the labelled images thereof into the same symmetric standard space, to achieve the registration from the acquired PET images and the labelled images to standard symmetric brain templates;
   (3) adopting a deep learning system based on symmetry, comprising following modules:
   3.1) a data preprocessing module:
   3.1.1) data enhancement: performing radial distortion and image intensity enhancement on the registered image and the label to obtain a newly generated image and label;
   3.1.2) image block division: performing image block division on enhanced image data, using a three-dimensional sliding window to divide left and right hemispheres L and R of the PET image into mirror image pairs of the image block, and dividing data of the mirror image pairs of the image block into a training set and a test set according to proportions; the training set and the test set all contain two types of PET image block data—epileptogenic focus and normal;
   3.2) a network building module: building a deep twin network SiameseNet, and this network contains two identical convolutional neural networks, a fully connected layer and an output layer; the SiameseNet inputs the mirror image pairs of a pair of image blocks to the two convolutional neural networks which share a weight parameter θ in each layer, to obtain a feature L_feature and a feature R_feature of two high-dimensional image, an absolute difference of the two high-dimensional image features is calculated: d=|L_feature−R_feature|, and it is transmitted to a multi-layer perceptron of the fully connected layer for probability regression, and the output layer uses a classification probability of a softmax regression function, that is, a probability that the image block carries the epileptogenic focus or is normal;
   3.3) a test image detection module:
   image classification: using the trained network to calculate a probability heatmap of the PET image of the test set, and using a logistic regression algorithm to classify the probability heatmap corresponding to each PET image, to obtain a classification result, that is, the normal PET image or the epileptogenic focus PET image;
   locating of the epileptogenic focus: performing bilinear interpolation on the probabilistic heatmap identified as the epileptogenic focus PET image, changing the probability heatmap to a size of the original image, and predicting a region larger than a probability threshold as the epileptogenic focus region.

2. The three-dimensional automatic location system for the epileptogenic focus based on the deep learning according to claim 1, wherein 1.1) in the process of acquiring the image, format conversion is performed on the acquired PET brain image, that is, the originally acquired image in a DICOM format is converted into an image in a NIFTI format.

3. The three-dimensional automatic location system for the epileptogenic focus based on the deep learning according to claim 1, wherein (2) in the image registration module, a Gaussian smoothing algorithm is used to reduce registration errors, the Gaussian smoothing process selects FWHM of full width at half maximum of the Gaussian function to be 5 to 15 mm, and Z-score normalization is performed on the smoothed image.

4. The three-dimensional automatic location system for the epileptogenic focus based on the deep learning according to claim 1, wherein 3.1.1) in the process of the data enhancement, radial distortion is specifically as follows: the radial distortion is that an image pixel point takes a distortion center as a center point, deviation is generated along a radial position, and a calculation process of the radial distortion is:

$$P_u = P_d + (P_d - P_c)(k_1 r^2 + k_2 r^4 + k_3 r^6 + \ldots),$$

where $P_u$ is a pixel point of the original image, $P_d$ is a pixel point of the distorted image, $P_c$ is a distortion center, $k_i (i=1,2,3 \ldots)$ is a distortion coefficient of the radial distortion, and r is a distance between $P_d$ and $P_c$ in a vector space.

5. The three-dimensional automatic location system for the epileptogenic focus based on the deep learning according to claim 1, wherein 3.1.1) in the process of the data enhancement is specifically as follows: the image intensity enhancement comprises filter processing, image noise-adding processing, and multiplicative and additive transformation of image gray values in the space, and a formula for the image intensity enhancement is:

$$P_a = g\_mult \times P_u + g\_add,$$

where $P_a$ is an image pixel point after the image intensity enhancement, g_mult is an image pixel point of a multiplicative Gaussian bias field, and g_add is an image pixel point of an additive Gaussian bias field.

6. The three-dimensional automatic location system for the epileptogenic focus based on the deep learning according to claim 1, wherein 3.1.2) in the division of the image block, resolution of each PET image data in the image data set is X×Y×Z pixels, a size of the sliding scanning window block is set to m×m×m, and a sliding step length is set to t, then the size of each image block is m×m×m, and for the left and right hemispheres of a PET image, it can be divided into $$\frac{\frac{X}{2} - m}{t} \times \frac{Y - m}{t} \times \frac{Z - m}{t}$$

pairs of image blocks.

7. The three-dimensional automatic location system for the epileptogenic focus based on the deep learning according to claim 1, wherein 3.2) in the network building module, each of the convolutional neural networks of the SiameseNet has a structure of ten layers, in which the first layer comprises one convolution layer, one batch normalization operation unit, one Relu function, and one pool layer that are connected in sequence; each of the second to the ninth layers is a ResBlocks, and each of the ResBlocks contains two convolution layers, two normalization operations and one Relu function that are connected in sequence; the tenth layer is one convolution layer, and the tenth layers of the two convolutional neural networks output and are connected to one fully connected layer for nonlinear transformation, dimensions of the fully connected layer vectors are 2048, 1024, 512 and 2 in sequence, and finally, one output layer is connected.

8. The three-dimensional automatic location system for the epileptogenic focus based on the deep learning according to claim 7, wherein 3.2) in the network building module, in the model training, a cross entropy function is used as a loss function of the network, and a calculation formula of the cross entropy Loss(a, b) is:

$$Loss(a, b) = -\Sigma_{i=1}^n a_i \ln b_i,$$

where n represents the number of samples, a is correct probability distribution, and b is probability distribution predicted by the network model;

standard stochastic gradient descent is used to update the weight parameter θ, and a formula thereof is:

$$\theta^k = \theta^{k-1} - \eta \frac{d}{d\theta^{k-1}} Loss(a, b),$$

where η is a learning rate, and $\theta^k$ is a k-th weight parameter.

9. The three-dimensional automatic location system for the epileptogenic focus based on the deep learning according to claim 1, wherein 3.2) in the network building module, in the SiameseNet network model, a calculation process of the convolution layer operation is:

$$output_{conv} = \frac{input_{conv} + 2 \times pad - kernal}{stride} + 1,$$

where $output_{conv}$ is the three-dimensional size of output image data of each of the convolution layer, $input_{conv}$ is a three-dimensional size of an input image, pad means to fill pixels around the image, kernal is a three-dimensional size of a convolution kernel, and stride is a step length of the convolution kernel;

for each of the convolution layers, the batch normalization operation is used, and a formula for the batch normalization operation is:

$$\widetilde{input_{norm}} = \frac{input_{norm} - \mu}{\sqrt{\sigma^2 + \epsilon}}, \text{ and}$$

$$output_{norm} = \gamma \widetilde{input_{norm}} + \beta,$$

where $input_{norm}$ is each batch data that is input, $\widetilde{input_{norm}}$ is normalized data, $output_{norm}$ is batch data output by the batch normalization operation, μ and σ are respectively mean and variance of each batch data, γ and β are respectively scaling and translation variables, and ε is a relatively small constant data added to increase training stability.

* * * * *